US009108138B2

(12) United States Patent
Hao et al.

(10) Patent No.: US 9,108,138 B2
(45) Date of Patent: Aug. 18, 2015

(54) ACCELERATED MIXED GAS INTEGRITY TESTING OF POROUS MATERIALS

(75) Inventors: Jibin Hao, Acton, MA (US); Salvatore Giglia, Norwood, MA (US); Michael Joens, Beverly, MA (US); Ronald Tuccelli, Winchester, MA (US)

(73) Assignee: EMD Millipore Corporation, Billerica, MA (US)

( * ) Notice: Subject to any disclaimer, the term of this patent is extended or adjusted under 35 U.S.C. 154(b) by 423 days.

(21) Appl. No.: 13/357,403

(22) Filed: Jan. 24, 2012

(65) Prior Publication Data

US 2013/0019658 A1    Jan. 24, 2013

Related U.S. Application Data

(60) Provisional application No. 61/435,623, filed on Jan. 24, 2011.

(51) Int. Cl.
*G01N 15/08* (2006.01)
*B01D 46/24* (2006.01)
*B01D 46/54* (2006.01)

(52) U.S. Cl.
CPC .......... *B01D 46/2411* (2013.01); *B01D 46/543* (2013.01); *G01N 15/082* (2013.01); *G01N 2015/084* (2013.01)

(58) Field of Classification Search
CPC .................. G01N 2015/084; G01N 2015/086; G01N 15/082; B01D 46/2411; B01D 46/543
USPC ............................................................ 73/38
See application file for complete search history.

(56) References Cited

U.S. PATENT DOCUMENTS

| | | | |
|---|---|---|---|
| 4,515,007 A | 5/1985 | Herman | |
| 5,282,380 A | 2/1994 | DiLeo et al. | |
| 5,457,986 A | 10/1995 | DiLeo et al. | |
| 5,581,017 A | 12/1996 | Bejtlich, III | |
| 5,789,024 A | 8/1998 | Levy et al. | |
| 6,324,898 B1 | 12/2001 | Cote et al. | |
| 6,568,282 B1 | 5/2003 | Ganzi | |
| 6,983,504 B2 | 1/2006 | Grummert et al. | |

(Continued)

FOREIGN PATENT DOCUMENTS

EP    0640822 A2    3/1995

OTHER PUBLICATIONS

International Search Report and Written Opinion received for PCT Patent Application No. PCT/US2012/022409, mailed on Aug. 22, 2012, 9 pages.
Knight et al., "New Integrity Test Method", 8th Annual Membrane Planning Conference, Newton, MA, 1990, pp. 357-366.

(Continued)

*Primary Examiner* — Peter Macchiarolo
*Assistant Examiner* — Natalie Huls
(74) *Attorney, Agent, or Firm* — EMD Millipore Corporation

(57) ABSTRACT

The invention relates to accelerated mixed gas integrity testing methods, devices, and systems for integrity testing wetted single and multi-layered porous materials, whereby the testing method is non-destructive to the porous materials being tested. The accelerated mixed gas integrity test method includes one or more of the following components: i) a permeate side gas purge component; ii) a permeate side volume reduction component; and iii) a permeate side circulation component. The invention is directed towards reducing the length of time necessary to complete the integrity testing of single and multi layered porous materials, elements and membranes.

22 Claims, 5 Drawing Sheets

(56) References Cited

U.S. PATENT DOCUMENTS

| | | |
|---|---|---|
| 7,501,061 B2 | 3/2009 | Wood et al. |
| 7,587,927 B2 | 9/2009 | Burke et al. |
| 7,592,178 B2 | 9/2009 | Ding et al. |
| 7,594,425 B2 | 9/2009 | Lewnard et al. |
| 2003/0159977 A1 | 8/2003 | Tanny et al. |
| 2008/0110243 A1* | 5/2008 | Burke et al. ............ 73/38 |
| 2009/0220940 A1 | 9/2009 | Lev et al. |
| 2010/0223980 A1 | 9/2010 | Burke et al. |

OTHER PUBLICATIONS

Phillips et al., "A Validatible Porosimetric Technique for Verifying the Integrity of VirRetentive Membranes", Biologicals, vol. 24, No. 3, Sep. 1996, pp. 243-253.

International Preliminary Report on Patentability received for PCT Patent Application No. PCT/US2012/022409, mailed on Aug. 8, 2013, 6 pages.

Meltzer, et al., "Filtration in the Biopharmaceutical Industry", Marcel Dekkar, Inc., New York, 1998, 69 pages.

\* cited by examiner

ACCELERATED MIXED GAS INTEGRITY TESTING OF POROUS MATERIALS

CROSS-REFERENCED TO RELATED APPLICATIONS

This application claims the benefit of U.S. Provisional Patent Application No. 61/435,623, filed on Jan. 24, 2011, the entire contents of which are incorporated by reference herein.

DESCRIPTION OF THE INVENTION

1. Field of the Invention

The invention relates generally to the field of validation testing of porous materials. In certain embodiments, the invention relates to validation testing porous materials using accelerated mixed gas integrity testing methods, devices and systems.

2. Background of the Invention

Porous materials play a significant role in a wide variety of industrial applications including processing, e.g. filtering, packaging, containing, and transporting manufactured goods and raw materials. The industrial settings in which they are used include the pharmaceutical and biotechnology industries; the oil and gas industries and the food processing and packaging industries, to name but a few.

In the pharmaceutical and biotechnology industries, as well as the food processing industry, porous materials (e.g., membranes and the like) are used as filtration devices to eliminate undesirable and potentially harmful contaminants from marketable end products. Quality control and quality assurance requires that these filtration devices comply with desired performance criteria. Integrity testing of porous membranes provides a means for ensuring that a particular device meets its desired performance criteria. Typically, in the case of porous membranes, integrity testing ensures that the membrane is free of defects (e.g., free of breaches in the membrane exceeding a desired size limitation) which would impair the membrane function and thus allow the end product to become contaminated with harmful or undesirable material.

Integrity tests suitable for ensuring the performance criteria of porous membranes, (e.g., porous membranes within filtration devices and the like) have been previously employed and include, for example, i) particle challenge test; ii) liquid-liquid porometry test; and iii) bubble point test, (see U.S. Pat. Nos. 6,983,504; 6,568,282; 5,457,986; and 5,282,380; as well as Phillips and DiLeo, 1996, Biologicals 24:243; Knight and Badenhop, 1990, 8$^{th}$ Annual Membrane Planning Conference, Newton, Mass.; Badenhop; Meltzer and Jonitz, 1998, Filtration in the Biopharmaceutical Industry. Marcel Dekkar, Inc., New York, N.Y.).

However, particle challenge tests, liquid-liquid porometry tests, bubble point tests, and air-water diffusion tests each have their own limitations.

For example, particle challenge tests are destructive to the membrane being tested and thus can only be performed once on a given specimen. Although it can be used for post-use integrity membrane testing, it is not suitable for pre-use validation, except for validating the performance of a membrane production lot. Lot validation, however, provides little assurance regarding the integrity of individual membranes within a production lot. Moreover, the test procedures and analysis can be difficult and complex.

The flow based tests, including the liquid-liquid porometry test and the bubble point test, do not provide a direct universal measurement of a porous membrane's retentive performance, but instead assess performance based on a correlation between integrity testing data (e.g., gas or liquid diffusion) and membrane retentive performance.

Some flow based tests are also limited in their sensitivity (e.g., size detection limit of a porous membrane's defects).

Additionally, flow based tests are limited to single layer membranes, thus defect(s) present in only one porous layer or membrane of a multilayered device are not detectable using flow based tests.

Binary gas integrity testing provides an alternative integrity test method suitable for ensuring the desired performance criteria of porous filtration membranes and oilers a method to detect defects, in porous filtration membranes.

Typically, in a binary gas membrane integrity test, two gases are compressed and fed to the feed side of a porous filter element (e.g., a membrane), wetted (e.g., wetted with water), whereby one of the gases permeates through the wetted water layer faster than the other gas. A portion of the feed gas is used as a sweep to maintain a constant gas composition on the feed side. A gas analyzer is used to monitor for a particular gas concentration in the permeate side until the gas concentration in the permeate side reaches steady state. The integrity of the porous filter element can then be determined by the final gas concentration in the permeate side.

In the binary gas integrity test method, the initial gas concentration in the permeate side of the porous filter element is not the same as the final steady state gas concentration. When testing the integrity of a porous filter element using the binary gas integrity test, it is desirable to be able to complete the test as quickly as possible. However, the rapidity of the test is constrained by the duration of time necessary to flush out the pre-existing gas present in the permeate side of the porous filter element.

For example, U.S. Pat. No. 7,594,425, titled "Methods and Systems for Integrity Testing of Porous Materials", and assigned to Millipore Corporation, teaches binary gas integrity testing methods wherein the determination of the equilibrium gas composition measured on the permeate side of a filtration membrane is delayed until the pre-existing gas has been flushed out of the system. The "flushout time" of the pre-existing gas depends on the gas diffusion flow rate from the feed side to the permeate side, and the downstream permeate side volume of the pre-existing gas. When the gas diffusion flow rate in the binary gas integrity test is small relative to the permeate side volume, the flushout time can significantly add to the total time required to complete the test, as well as increase the consumption of the feed gas used in order to complete the test.

A need therefore exists for an integrity test of porous materials suitable for a variety of porous materials, including porous single layer materials, porous materials having a multi-layered configuration, porous membranes and filters just to name a few, which provides a non-correlative universal standard for assessing porous materials performance and integrity. It would be desirable to provide an integrity test that is relatively fast, sensitive, non-destructive to the porous materials being tested, inexpensive and easy to execute.

Additionally, it would be desirable to provide an integrity test that allows for the characterization of the size and density of any defect(s) in a porous filter material layer(s), porous Membrane or porous element, in order to determine if a desired performance criteria of the porous material has been compromised by the defect, or if the defect is inconsequential in terms of performance criteria.

Desirably, such an integrity test would provide a faster determination of the integrity of a porous material layer(s) than using current integrity testing methods, thereby resulting in lower testing costs and greater productivity. Desirably, such an integrity test would allow for the simultaneous measurement of the air diffusion flow rate of the porous material being tested. A need also exists for a device or device and system which can implement such porous filter material layer(s), membrane(s) or element(s) integrity testing methods.

SUMMARY

In response to the above needs, the present invention provides an accelerated mixed gas integrity test method, system and device for integrity testing single and multilayered porous materials that is simple, rapid, repeatable and non-destructive to the porous materials being tested. The present invention is directed towards reducing the length of time necessary to complete the integrity testing of single and multilayered porous materials, elements and membranes.

In certain embodiments, the invention provides an accelerated mixed gas integrity testing device having a housing for receiving single and multilayered wetted porous material samples (e.g., porous membranes, layers, sheets, filter elements, and the like) to be integrity tested. Once disposed within the device housing, the wetted porous sample has a feed side and a permeate side. On the permeate side of the wetted porous sample, the housing is in fluid communication with i) a process condenser, ii) an optional hydrophobic membrane to prevent free water from entering the $O_2$ analyzer, iii) an optional desiccant to prevent water vapor from entering the $O_2$ analyzer iv) an absolute pressure transmitter, v) a thermocouple probe, vi) a gas recirculation component, vii) a gas pressure relief component to maintain constant permeate side gas pressure, viii) gas composition analyzer, and ix) a five port switching valve.

In other embodiments, the present invention provides a method for determining the integrity of single and multilayered wetted porous material samples (e.g., porous membranes, layers, sheets, filter elements, and the like) housed in an accelerated mixed gas integrity testing device using an accelerated mixed gas integrity test method.

In still another embodiment the invention provides a system for assessing the integrity of single and multilayered porous materials using accelerated mixed gas integrity testing methods and devices provided herein.

In yet another embodiment, the invention provides methods for locating at least one defect in single and multilayered porous materials using the accelerated mixed gas integrity testing methods provided herein.

In further embodiments, the invention provides methods for characterizing a defect in single and multi-layered porous materials using the accelerated mixed gas integrity testing methods provided herein.

In still another embodiment the invention provides a method of assessing the integrity of one or more porous liquid filtration membranes comprising at least one defect using the accelerated mixed gas integrity testing methods provided herein.

In still other embodiments, the invention provides methods for assessing the integrity of single and multilayered porous materials independent of specific characteristics of the porous materials using the accelerated mixed gas integrity testing methods provided herein, such that the integrity testing methods are independent of one or more of the following:
 i) the physical properties of the single and multilayered porous materials being tested;
 ii) the volumetric changes in the single and multilayered porous materials and/or the housing holding the porous materials being tested; and
 iii) the surface area of the single and multilayered porous material being tested.

In some embodiments, the invention provides a universal standard for assessing the integrity of a single porous material, such as a porous membrane or porous layer.

Certain embodiments of the invention provide a method for determining the integrity of single and multilayered porous membranes, such as liquid filtration elements, by monitoring the direction of the concentration trend (i.e., stable, increase, or decrease) of a particular gas relative to the permeate side baseline flush gas concentration.

Some embodiments of the invention provide a method of integrity testing single and multilayered porous materials based on the concentration of one or more gases in the permeate.

Certain embodiments of the invention provide an accelerated mixed gas integrity test method independent of the gas diffusion flow rate through a wetted single or multilayered porous materials In certain embodiments the present invention provides an accelerated mixed gas integrity test method that includes one or more of the following components:
 i) a permeate side gas purge component;
 ii) a permeate side volume reduction component located within the housing; and
 iii) a permeate side circulation component.

Other embodiments of the invention provide a system for assessing the integrity of single and multilayered porous materials using the accelerated mixed gas integrity test methods and devices provided herein which may further include one or more sensor devices. (e.g., a device to sample and/or analyze permeate side gas composition), one or more computers, (e.g., a personal computer), internet access, one or more networks, and/or one or more databases.

In still another embodiment, the invention provides an accelerated mixed gas integrity test method for assessing the detect size distribution of a single and multilayered porous material by increasing or decreasing the feedside gas pressure in a stepwise manner.

Other embodiments of the invention provide an accelerated mixed gas integrity testing method for assessing the integrity of single and multi-layered porous materials using the gas mixture composition present in the permeate.

Additional objects and advantages of the invention will be set forth in part, in the description which follows, and in part will be apparent from the description, or may be learned by practice of the invention. The objects and advantages of the invention will be realized and attained by means of the elements, processes, systems and combinations particularly pointed out in the appended claims.

The specific embodiments described herein are offered by way of example only and are not meant to be limiting in any way. It is to be understood that both the foregoing general description and the following detailed description are exemplary and explanatory only and are not restrictive of the invention, as claimed.

BRIEF DESCRIPTION OF THE DRAWINGS

In general, each of the Figures provide schematic representational illustrations of embodiments of the invention and its components. The relative location shapes, and/or sizes of objects are exaggerated and/or simplified to facilitate discussion and presentation herein.

FIG. 4A illustrates the described behavior for a single layered porous material device. FIG. 4B illustrates the described behavior for a multilayered porous material device.

DESCRIPTION OF THE EMBODIMENTS

Figure 1:
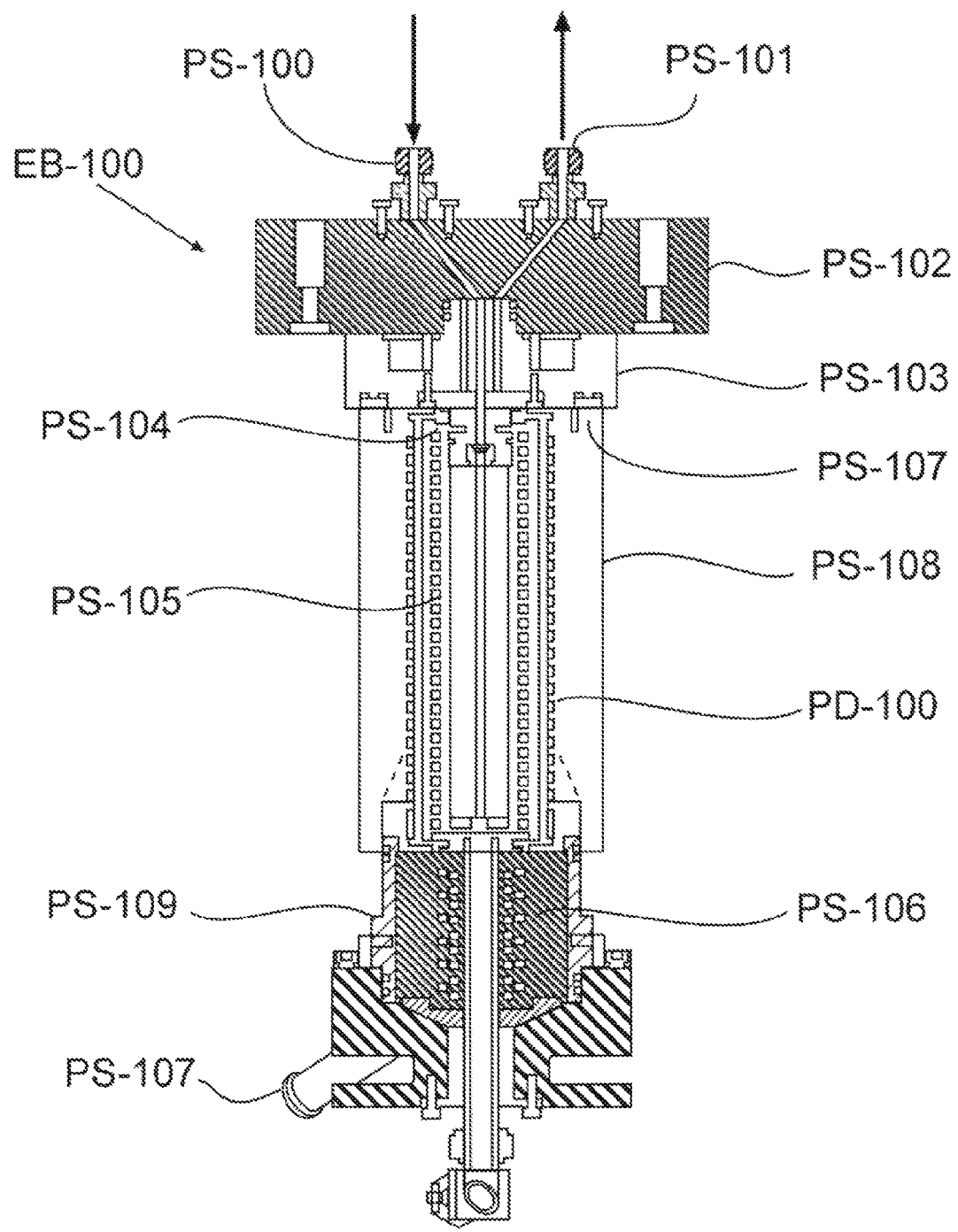
FIG. 1 is a schematic cross section of an accelerated mixed gas integrity testing system for a porous material according to an embodiment of the invention as taught herein.

All publications, patents and patent applications cited herein, whether supra or infra, are hereby incorporated by reference in their entirety to the same extent as if each individual publication, patent or patent application was specifically and individually indicated to be incorporated by reference.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about".

Accordingly, unless indicated to the contrary, the numerical parameters set forth in the following specification and attached claims are approximations that may vary depending upon the desired properties sought to be obtained by the present invention. At the very least and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass all subranges subsumed therein. For example, a range or "1 to 10" includes any and all subranges between (and including) the minimum value of 1 and the maximum value of 10, that is, any and all subranges having a minimum value of equal to or greater than 1 and a maximum value of equal to or less than 10, (e.g., 5.5 to 10).

Before describing the present invention in further detail, a number of terms will be defined. Use of these terms does not limit the scope of the invention but only serve to facilitate the description of the invention.

As used herein, the singular forms "a", "an", and "the" include, plural referents unless the context clearly dictates otherwise.

The expression "integral" as used herein when referring to porous materials such as a porous single layer or porous membrane, porous multilayers, or a plurality of porous membranes, means a non-defective porous material.

The expression "non-integral" as used herein when referring to porous materials such as a porous single layer or porous membrane, porous multilayers, and a plurality of porous membranes means a defective porous material. Examples of defects in a porous layer or membrane include, but are not limited to, oversized pores, improper bonding (e.g., delamination or separation) between a plurality of porous layers or membranes that are bonded together to form a multilayer element, and defects on the porous layer or porous membrane.

The expression "porous material", as used herein, includes, but is not limited to, one or more porous membranes, sheets, rods, discs, tubes, layers, filters, filter elements, filtration media, containers, bottle caps, cylinders, hoses, cassettes, columns, chips, beads, plates, monoliths, and combinations thereof. In addition the porous materials may be pleated, flat, and combinations thereof.

The expression "universal criteria" for a single porous layer or membrane, as used herein, means that the test results provide a direct measurement of performance criteria not dependent on correlation or extrapolation of porous material properties for single layers or membranes of porous materials. The resulting value obtained from the test is thus independent of the properties porous materials.

Method Conditions

In certain embodiments, the accelerated mixed gas testing methods as taught herein use at least two gases having differing permeabilities in the liquid used to wet the porous material for directly determining the integrity of a porous material.

The conditions under which the accelerated mixed gas testing methods of the invention are practiced may be chosen by the skilled artisan. As an example, the methods of the invention may be practiced at a temperature ranging from about 0° C. to about 100° C., about C to about 60° C., about 10° C. to about 50° C., and about 15° C. to about 30° C. In other embodiments the invention is practiced at a temperature of about 20° C. In another embodiment the invention is practiced at a temperature of about 4° C.

When the accelerated mixed gas integrity test methods provided herein are run, the gas pressure on the feed side of the porous material is greater than the gas pressure on the permeate side of the porous material, and the gas pressure on the feed side of the of the porous material is less than the bubble point of the of the porous material.

The skilled artisan will understand that in practicing the accelerated mixed gas integrity testing methods as taught herein, variables such as operating feed gas pressure may be varied to meet the porous materials requirements, sensitivity limits, and operator convenience.

Nonlimiting examples of the feed gas pressure include ranges from about 1 PSI to about 100 PSI; from about 10 PSI to about 70 PSI; from about 5 PSI to about 60 PSI; and from about 20 PSI to about 45 PSI.

In other embodiments the invention is practiced at a feed gas pressure of about 30 to about 50 PSI. In other embodiments the invention is practiced at a feed gas pressure of about 50 PSI. While in additional embodiments the invention is practiced at a feed gas pressure of about 30 PSI. While in other embodiments the invention is practiced at a feed gas pressure of about 15 PSI.

The percentage of each gas in the feed gas mixture may be chosen by the skilled artisan. As an example, when two gases are used the first gas may be used in a percentage volume ranging from about 0.001% to about 99.999%, and the second gas may be present in a percentage volume ranging from about 0.001% to about 99.999%.

The skilled artisan will understand that in practicing the accelerated mixed gas testing method as taught herein, variables such as operating pressure, liquid composition, gas species and gas composition may be varied to meet the porous materials' requirements, sensitivity limits, and operator convenience. It will also be understood by the skilled artisan that functional properties of the porous material (e.g., retention of a target species such as bacteria, viruses, mycoplasmas, and the like) may be correlated with the porous material's integrity measurements determined in accordance with the methods, devices, and systems provided herein.

Certain embodiments of the accelerated mixed gas integrity test methods of the invention as taught herein provide a method of assessing the integrity of a porous layer(s), porous membrane(s) or porous materials. The integrity test methods may be performed before or after the porous layer, membrane or material is used for its intended purpose, and may be repeated more than once, if desired.

The accelerated mixed gas integrity testing methods of the invention as taught herein allows the skilled artisan to choose the combination of liquids, gases and porous materials depending on individual needs. Moreover, the integrity test methods provided herein increase the sensitivity of assessing the integrity of porous materials compared to previously described air diffusion test methods. Thus certain embodiments of the accelerated mixed gas integrity testing methods of the invention provide a method of detecting defects in porous layer(s), membrane(s) or material(s) that range from about 1 to 100, about 2 to 50, and about 10 to 50 times smaller than the defects detected by air-water diffusion tests alone.

For a variety of porous materials the effect of defects on the retentive properties of the porous materials may be assessed.

When it is desirable to quantify detect size and/or defect population density in porous materials the integrity testing methods provided herein may be practiced under gas pressure ramping modes such that a plurality of data points are measured as gas pressure is increased, including, for example, permeate side flow rate.

Additional embodiments of the accelerated air binary gas test methods provide methods for quantifying defects in the porous materials as a function of size. The skilled artisan will appreciate that detection ranges will be influenced by, for example, the area of the porous materials used, the choice of gases, the choice of wetting fluid, and testing pressure(s).

Porous Materials

The integrity testing methods of the present invention can be used with any filter media of any size that is capable of being integrity tested using gases or liquids. The porous materials selected to be integrity tested depends upon the application, desired filtration characteristics, particle type and size to be filtered, and the flow desired.

The integrity of one or more layers or membranes of porous materials may be assessed using the accelerated air binary gas integrity testing methods, devices and systems provided herein.

The porous materials may comprise organic and/or inorganic materials.

In the addition, the porous materials may comprise a hydrophilic material, a hydrophobic material, an oleophobic material, an oleophilic material or any combination thereof. The porous materials may comprise a polymer and/or copolymer and the polymers and copolymer may be crosslinked.

The porous materials may comprise any suitable material, including, but not limited to polymers such as polyolefins including polyethylene (e.g., ultrahigh molecular weight polyethylene), polypropylene, EVA copolymers and alpha polyolefins, metallocene olefinic polymers, PFA, MFA, polytetrafluoroethylene (PTFE), polycarbonate, vinyl copolymers such as PVC, polyamides (e.g., nylon), fluorocarbon (e.g., poly (tetrafluoroethylene-co-perfluoro(alkylvinylether)), polyesters, cellulose, cellulose acetate, regenerated cellulose, cellulose composites, polysulfone, polyethersulfone (PES), polyarylsulfone, polyphenylsulfone, polyacrylonitrile, polyvinylidene fluoride (PVDF), and blends thereof. In addition polymers, the porous materials may also comprise glass fibers, ceramics, metals, and combinations and/or mixtures thereof.

In certain embodiments the porous material includes for example, a porous liquid filtration membrane capable of excluding solutes based on one or more properties of the solutes (e.g., the size of the solutes).

In certain embodiments, the pores of the porous liquid filtration membrane may be too small to allow the passage of solute particles in a solution, having a specific size (e.g., diameter or a particular molecular weight). In addition, some or all of the solute particles may or may not be dissolved in the solution.

In certain embodiments, the porous material may be in the form of a single membrane or a plurality of membranes. The porous materials may, for example, be a hollow fiber, tubular format, flat plate, disk, or spirally wound.

The porous materials can be contained in a filtration device housing (e.g., a cylinder, a cassette and the like).

The pore structure in the porous membrane may be symmetric or asymmetric.

The porous membrane may be used in liquid filtration in order to separate or remove from a filtered liquid any unwanted materials including contaminants, infectious microorganisms, viruses, and mycoplasmas, environmental toxins and pollutants.

In certain embodiments, where the porous material is comprised of more than one layer or membrane, an outlet or port may be provided to obtain samples from the interstitial space or spaces formed therein.

The porous materials include, by way of example only, microporous membranes, nanofiltration membranes, ultrafiltration membranes, microfiltration membranes, and reverse osmosis membranes.

Liquids and Wetting Agents

Any suitable liquid can be used as a wetting agent for the porous material being integrity tested in accordance with the inventions as taught herein. Selection of a wetting agent is within the ordinary level of skill of the artisan and may be determined based on chemical and physical properties of the porous material. Porous materials vary in terms of their wettability, which is often expressed in terms of the contact angle.

The accelerated mixed gas integrity test methods of the invention can be adapted for hydrophobic membranes, for example, by selecting non-aqueous solvents or prewetting it with low surface tension fluids such as, for example a mixture of 70% isopropyl alcohol and 30% water, and exchanging the low surface tension fluid with water.

A skilled artisan will thus understand that a liquid may be selected by considering the chemical properties of the porous materials being integrity tested. As a nonlimiting example, where the porous material is comprised of a hydrophilic material, a suitable liquid includes water or a solution comprised of water. The solution may be, for example, aqueous solutions containing salts and oxygenated hydrocarbons such as aldehydes or alcohols, or neat alcohols such as isopropyl alcohol.

Where the porous materials include a hydrophobic material, a suitable liquid includes, for example, any organic solvent such as dodecane, perfluorinated compounds, carbon tetrafluoride, hexane, acetone, benzene, and toluene.

Gases

The accelerated mixed gas test method taught herein provides flexibility with regard to choices of liquid and gas components and compositions. In certain embodiments it is desirable to choose feed gases which have differing permeabilities in the liquid chosen to wet the porous material being integrity tested. In some embodiments more than two gases may be used.

In general it is useful to choose gas combinations with large differences in gas permeability through the wetting liquid, and gas compositions that have one species in trace concentration and the other present as the bulk species. For example, feed gas compositions can vary from approximately 0.001 to 1 for binary gas mixtures using common species such as nitrogen, oxygen, carbon dioxide, helium, hydrogen, and hexafluoroethane, with water as the pore-filling liquid wetting agent for the porous material.

For tests with hydrophobic liquids, such as dodecane, gas pairs could include high permeability gases such as ethane, propane, and butane paired with low-permeability gases such as He, $H_2$, and $N_2$. In certain embodiments at least one of the gases may be Freon, (e.g., hexafluorobthane). In other embodiments at least one of the gases is a noble gas. In still other embodiments, at least one of the gases is $CO_2$.

In further embodiments at least one of the feed gas components is comprised of a mixture of gases. Where each of the gases components are provided as a mixture of more than one gas, the mixture may be premixed before contacting the porous material. Wide ranges of gas composition are available; for example feed gas mixtures of hexafluoroethane in $CO_2$ can vary from less than 0.1% to more than 99.9%.

In certain embodiments, the feed gas composition comprises compressed air consisting of a mixture of $O_2$ and $N_2$. The skilled artisan will be able to choose appropriate gases and gas mixtures based upon known properties.

Systems and Devices

Figure 2:
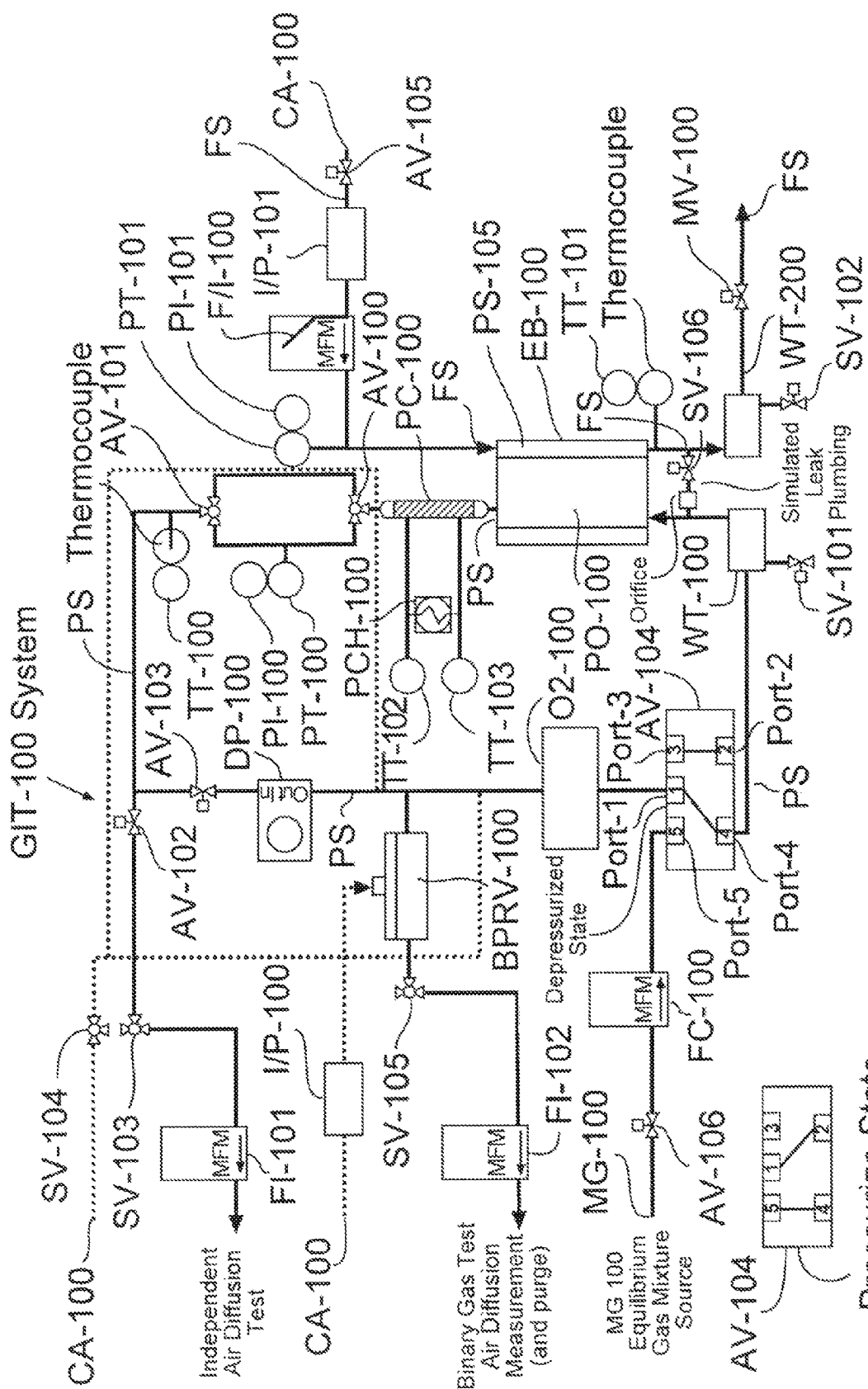
FIG. 2 is a schematic diagram of an accelerated mixed gas integrity testing system (GIT-100) according to an embodiment of the invention as taught herein.
Figure 3:
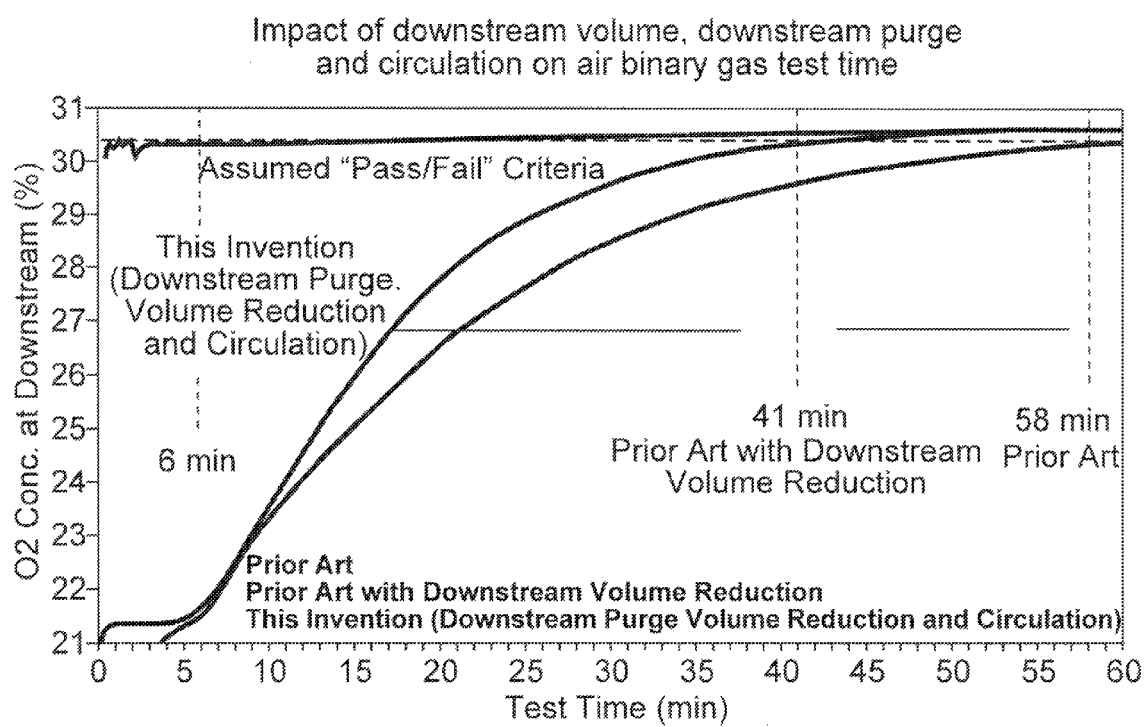
FIG. 3 is a graph showing the impact of three variable conditions (i.e., permeate side gas volume, permeate side gas purge, and gas circulation) on binary gas integrity testing time according to an embodiment of the invention as taught herein, compared with prior art binary gas test methods.

The integrity test system (GIT-100) depicted in schematic form in FIGS. 1 and 2 includes a device (EB-100) having a device housing (PS-108, PS-109) suitable for receiving a porous material sample (e.g., a porous membrane, or a filtration element) (PD-100) being integrity tested. In certain embodiments, the invention provides an accelerated air binary gas test system (GIT-100) suitable for determining the integrity of the porous material sample (PD-100).

As depicted in FIG. 2 the feed gas source (CA-100) includes a binary gas source such as compressed air, and the like. Alternatively, and or in addition thereto, the device (EB-100) comprises one or more valves, (e.g., two way valves, three way valves, four way valves) to control the flow of gasses through the system. In one embodiment for integrity testing a porous sample material (PD-100), the porous sample is first wetted with a liquid such as water, then placed inside a device housing (PS-108, PS-109). In certain embodiments of the invention a dry porous sample is placed inside a porous material sample housing (PS-108, PS-109) and wetted, with a liquid such as water, in place with the housing.

The feed side of porous sample housing (EB-100) is in fluid communication with a feed gas source (CA-100), a two way valve (AV-105), an electropneumatic regulator (I/P-101), a mass flow meter (FI-100), an absolute pressure transmitter (PT-101), a temperature transmitter (TT-101), a water trap, a drain valve (SV-102), and a flow control valve (MV-100)

A feed gas, such as compressed air, where $O_2$ and $N_2$ are nonlimiting examples of a binary gas pair that can be used, from source (CA-100) is fed through a valve (AV-105), into the feed side (FS) of housing (EB-100), and through the flow control valve (MV-100) to atmosphere.

An ectropneumatic regulator (I/P-101) is used to control the absolute pressure (PT-101) on the feed side (FS) of the wetted porous sample (PD-100) in housing (EB-100) to a constant ratio with respect to the absolute pressure (PT-100) measured on permeate side (PS) of the wetted porous material sample housing (EB-100). Pressure is controlled such that the feed side (FS) absolute pressure (PT-101) is set to a value equal to a pressure ratio factor ("PR") multiplied by the measured absolute pressure (PT-100) on the permeate side (PS) of the wetted porous sample (PD-100) in housing (EB-100) (e.g., feed side pressure is about two times the permeate side absolute pressure). Suitable values for the pressure ratio factor ("PR") include, but are not limited to values ranging from about 2 to about 10, including values such as 2, 3.5, and 10.

A flow control valve (MV-100) (e.g., a two way valve) is adjusted on the feed side (FS) of the test system (GIT-100) to the desired feed side sweep flow rate to maintain constant feed side gas concentration over the wetted porous sample (PD-100). Feed side flow rate is set such that the actual flow (FI-100) is equal to a flow ratio factor ("FR") multiplied by the measured permeate side flow (FI-102) (e.g., feed side flow rate is 200 times the permeate flow rate). Suitable values for the flow ratio factor include, but are not limited to values ranging from about 200 to about 1000, including values such as 200, 350, and 1000.

The permeate side of the wetted porous sample housing (EB-100) is in fluid communication with a process condenser (PC-100), an absolute pressure transducer (PT-100), a temperature transmitter (TT-100), a two way flush valve (AV-102); a two way shutoff valve (AV-103), a diaphragm compressor (DP-100), a precision back pressure regulating valve (BPRV-100), an $O_2$ analyzer (O2-100), a five port switching valve (AV-104), a water trap (WT-100) and a two way drain valve (SV-101).

In order to prepare the permeate side of the binary gas test equipment (GIT-100) for an accelerated integrity test, the existing gas of near atmospheric concentration is flushed out and replaced with a gas equal to or near to the expected equilibrium concentration for the porous material device being tested under the test conditions selected (feed side gas composition, pressure ratio, flow ratio, etc.).

A two way valve (SV-101) is opened on the permeate side (PS) of the binary gas test system (GIT-100) to allow water to drain. Once drained, the valve (SV-101) is closed. The five port switching valve (AV-104) is adjusted such that port 5 and port 4 connect, and port 1 and port 2 connect. The two way flush valve (AV-102) and the two way shutoff valve (AV-103) are opened. The diaphragm compressor (DP-100) is turned on. Excess flow is purged through the back pressure regulating valve (BPRV-100) and a constant stable gas flow is delivered to the $O_2$ analyzer (O2-100).

The equilibrium flush gas mixture source (MG-100) is charged to the inlet side of a mass flow controller (FC-100) where the desired flush gas flow rate is set. The Bush gas flows from the mass flow control valve (FC-100), through the 5-port switching valve (AV-104), into the permeate side of the porous material sample (PD-100), and through the process condenser (PC-100). Most of the flush flow is discharged to atmosphere through valve (AV-102); but a portion flows through the diaphragm compressor (DP-100), into the $O_2$ analyzer (O2-100), and is discharged to atmosphere through port 2 of the 5 port switching valve (AV-104). The flush gas flow rate can be optimized for the volume of the permeate side (PS) loop of the binary gas test equipment (GIT-100). The permeate side (PS) loop flush is considered complete when the reading on the $O_2$ analyzer (O2-100) is stable.

At the completion of the permeate side (PS) flush, the flush gas flow rate is ramped down to zero flow using control valve (FC-100). The permeate side loop (PS) valves are set to circulate the permeate side gas through the permeate side of the porous material sample (PD-100) and the $O_2$, analyzer (O2-100) for the duration of the test.

Gas from the permeate side (PS) of the porous material (PD-100) circulates for the duration of the integrity test. Flush valve (AV-102) is closed, shutoff valve (AV-103) is open, and the diaphragm compressor (DP-100) is on. Excess flow, resulting from a defect leak and/or diffusive flow from the feed side (FS) of the porous material sample (PD-100) to the permeate side (PS) of the porous material sample (PD-100), is purged through the backpressure regulating device (BPRV-100) to atmosphere. A stable flow is driven through the $O_2$ analyzer (O2-100) and into the five port switching valve (AV-104) where port 1 and port 4 connect; and port 3 and port 2 connect. The sample stream then passes through a water trap (WT-100) and hack into the permeate side (PS) of the porous material sample (PD-100).

Porous material sample integrity can be judged by one or any combination of the following: (i) the absolute concentration of permeate side (PS) recirculation gas measured at a specific test time, and (ii) the slope of the concentration of permeate side (PS) recirculation gas over specific test time period.

The accelerated mixed gas integrity test system (GIT-100) provided herein reduces binary gas integrity testing time and includes, in certain embodiments, one or more of the following components:

(i) a porous sample permeate side gas purge component (e.g., a pressure relief system (BPRV-100)) which removes the excess gas in the permeate side circulation loop and brings the gas concentration in the permeate to the equilibrium concentration or near to the equilibrium concentration for the porous material being tested under the test conditions selected (feed side gas composition, pressure ratio, flow ratio, etc.):

(ii) a porous sample permeate side (PS) volume reduction component (e.g., a solid polymer cylinder insert (PS-105)) located within the housing (EB-100) for downstream permeate side (PS) volume reduction; and/or iii) a porous sample permeate side (PS) circulation component (e.g., recirculation compressor (DP-100)).

Permeate Side Gas Purge Component

In certain embodiments, the present invention provides an accelerated binary gas integrity test method having a permeate side (PS) gas purge component which removes the excess gas in the permeate and brings the gas concentration in the permeate to equilibrium or near to equilibrium for the porous material (PD-100) being tested under the test conditions selected (feed side gas composition, pressure ratio, flow ratio, etc.).

In one embodiment of the accelerated air binary gas integrity test system (GIT-100) according to this invention, $O_2$ enriched air having the desired $O_2$ concentration is introduced through the flow path created by port 5 and port 4 of five port valve (AV-104) to flush out the pre-existing permeate side gas and establish a baseline permeate side (PS) gas concentration.

Port 1 and port 2 of five port valve (AV-104) are connected and open to the atmosphere to vent the excess gas. Valve (AV-102) can be opened to allow higher flush gas flow rates. At completion of the gas flush, the five port switching valve (AV-104) is set such that port 1 and port 4 connect to create a flow path; and port 3 and port 2 connect to create a flow path. Permeate side (PS) gas is circulated through the $O_2$ analyzer (O2-100) by a diaphragm compressor (DP-100).

The air diffusion how rate can be measured during an accelerated binary gas test by connecting a mass flow meter (FI-102) to the outlet of the pressure relief system (BPRV-100).

The equilibrium $O_2$ permeate concentration for an integral porous filter, membrane, or the like, is about 30.6%, at about 54.8 psia (pounds per square inch absolute) feed side (FS) pressure and about 14.8 psia permeate (PS) pressure.

Permeate Side Gas Recirculation Component

In certain embodiments the present invention provides an accelerated binary gas integrity test method having a permeate side circulation component.

Gas circulation may be accomplished using a compressor (DP-100) in fluid communication with housing EB-100 and the porous material (PD-100) being integrity tested. In certain embodiments the benefits of gas circulation include reduced length of testing time, as well as economical and environmental in that it limits amount of reagents used. Gas circulation eliminates the need to achieve a steady state and thus provides a more rapid result compared to previously known integrity tests.

In addition, the location of the defect or defects in the porous sample material (PD-100) being tested can effect the time it takes to complete the integrity test. For example if the defect is at the bottom of a porous material, such as located near the permeate outlet end (PS-101) as depicted in FIG. 1, the integrity test will take longer to complete than if the defect was located nearer the permeate inlet end (PS-100), also depicted in FIG. 1. However, wherever the defect or defects may be located in the porous material being tested, the test time will be reduced using the accelerated air binary gas integrity test method as taught herein, compared to using the air diffusion test or previously known binary gas integrity test methods.

Moreover, the accelerated air binary gas integrity test method as taught herein may be easily adapted to accommodate virtually any type of detector known in the art, and thus in certain embodiments the invention may avoid the use of cumbersome detection means requiring a direct line of sight (e.g., a photo acoustic detector). The accelerated air binary gas integrity test method as taught herein may allow for detection of smaller defects compared to previously described techniques.

Permeate Side Volume Reduction Component

As depicted in FIG. 1, certain embodiments the present invention provide an accelerated binary gas integrity test method having a permeate side (PS) volume reduction component (PS-105) located within the housing (EB-100) for permeate side volume reduction. In certain embodiments of the invention the permeate side volume reduction component (PS-105) may incorporate an axial bore to accommodate a leg of the permeate circulation loop flow path.

In addition, housing (EB-100) may have located therein a solid component insert, such as a cylinder (PS-105) or cylinder shaped component for example, as depicted in FIG. 1. The solid component insert (PS-105) can be fabricated from a polymer or other solid material to provide permeate side (PS) volume reduction. The insert (PS-105) can take on various non-limiting shapes, so long as the insert takes up the desired amount of space within the housing (EB-100) in order to provide the appropriate amount of volume reduction on the permeate side (PS) as determined by the practitioner.

In order to reduce the length of time required to complete the integrity testing of porous materials, such as typically experienced when integrity testing porous materials using known binary gas integrity testing methods, the permeate side pre-existing gas is first flushed with a gas composition at the predicted equilibrium concentration for porous material device (PD-100) being tested, or near to the predicted equilibrium concentration for porous material device (PD-100) being tested under the test conditions selected (feed side gas composition, pressure ratio, flow ratio, etc.). Next, the concentration of a specific gas component in the permeate side gas circulation loop (e.g., $O_2$) is monitored and the integrity of the porous material (PD-100) can be determined by the direction of the concentration trend (i.e., stable, increase, or decrease) for the particular gas (e.g., $O_2$) being monitored relative to the permeate side baseline flush gas concentration.

For example, in the binary gas integrity testing methods as taught in U.S. Pat. No. 7,594,425, the determination of the equilibrium gas composition measured on the permeate side of a membrane is delayed until the pre-existing gas has been flushed out of the system. The "flushout time" of the pre-existing gas depends on the permeate gas rate and the permeate side volume of the pre-existing gas. If the permeate flow rate is small relative to the permeate side volume, the flushout time can significantly acid to the total length of time required to complete a test time run, and consumption of feed gas.

Multilayered Membrane Devices

The accelerated air binary gas integrity test methods, systems and devices provided herein can perform integrity testing of porous multi-layered devices. Such multi-layered devices include devices comprised of more than one layer or membrane of porous material, which in certain embodiments may be configured or contained within a housing, cartridge and the like. The multilayered device may comprise 2, 3, 4, or more layers or membranes of porous material. The first porous layer of the multi-layered device may be the layer which is first contacted by a liquid sample entering the device. The last porous layer of the multilayered device may be the layer from which the liquid sample exits the device.

In some embodiments the multi-layered device may comprise a spacer (not shown) placed between adjacent or stacked layers of porous materials and which may facilitate integrity testing of the multi-layered device. The spacer may, for example, be a porous non-woven support.

In other embodiments, the multi-layered device does not include a spacer between the layers of porous material. In some embodiments, the layers of porous material may be stacked such that the layers are in close proximity to each neighboring layer.

In some embodiments the stacked layers of porous material may be contiguous with the neighboring layer. Air or gas pockets may spontaneously form between the layers of porous material in certain embodiments.

In other embodiments (e.g., where at least one layer of the device comprises an asymmetric membrane) air or gas pockets may form within at least one layer of the multilayer device. The air or gas pocket may form in a membrane which is highly porous, such as a microfiltration membrane.

In certain embodiments multiple layers of porous material stacked contiguously with the neighboring layer may advantageously serve to maintain the retentive capability of the device. For example, a breach or defect in one layer of porous material within a device wherein the layers of porous material are in close proximity may have only a minimal effect on the retentive capability of the device.

The invention also provides a system for assessing the integrity of a porous material. The system comprises the integrity testing device described above and further comprise a plurality of gases and additional sensor devices (e.g., a device to sample and/or analyze permeate flow). Choosing an additional sensor device is well within the capability of the skilled artisan. Suitable sensor devices may include a mass spectrometer, a gas chromatography column, infrared detector, an ultra-violet detector, a Fourier transform infrared detector, a volumetric bubbler/titrator. Since the gas composition can vary over four (4) orders of magnitude, it is desirable to use a detector that has a wide operating range. The system may optionally include a computer, e.g. a personal computer. The computer may be used to control automation of the test and may also be used to store and/or analyze data.

The accelerated air binary gas test methods of the invention taught herein can establish a universal a priori criterion for a single layer or a membrane integrity testing. Other porous membrane integrity tests, such as the air-water test, CorrTest™ (available from EMD Millipore Corporation, Billerica, US) rely on correlations between the test measurements and independent retention tests to establish the integrity criterion for the test. The precision of the correlation depends on the inherent variability of the test and membrane materials, and must be revalidated whenever significant changes are made to the membrane or test methods, materials, hardware, etc.

Using the accelerated air binary gas test methods as taught herein, the criteria for absolute, integrity for a single layer or a membrane can be established independent of any characteristic regarding the membrane structure, retention test methods, etc. By way of non-limiting examples of factors that determine the criterion of membrane integrity are the gas composition, choice of liquid use to wet the membrane (i.e., the wetting liquid) and gas pressure ratio.

Permeate Purge Gas Composition Determination

One advantage of the accelerated air binary gas integrity test methods taught herein over known air-water diffusion test methods is its invariance to many test and porous material properties. Air-water diffusion test results can vary with changes in properties such as porosity and tortuosity of the porous membrane. In contrast, the mixed gas integrity testing methods provided herein produce results based on the gas composition. As a result, the accelerated air binary gas test methods provided herein can provide a universal standard for assessing the integrity of single layer porous materials, membranes, filters and the like.

For a binary gas mixture, the equilibrium gas composition of the permeate gas can be predicted using the following equation:

$$\frac{y_p}{1-y_p} = \frac{\alpha(x_0 - Pr y_p)}{1 - x_o - Pr(1 - y_p)}$$

Where $y_p$ is the permeate concentration of the faster permeating gas, $\alpha$ is the ratio of gas permeabilities through the wetting liquid, $x_o$ is the outlet concentration of the faster permeating gas on the inlet side of the membrane, and Pr is the ratio of absolute pressure on the inlet side of the membrane to the absolute pressure on the permeate side of the membrane. If the feed flow rate is set to a value that is much greater than the permeate flow rate, then the outlet concentration on the high pressure side can be approximated as being equal to the inlet concentration. Note that permeate side concentration does not depend on specific characteristics of the porous material such as porosity, tortuosity, and thickness of the wetting fluid to name a few. Nor is the permeate gas composition of an integral device dependent on flow properties or the surface area of the porous material being tested.

A leak from the inlet side of the membrane to the permeate side of the membrane will cause a change in the permeate side gas concentration. Therefore a deviation in permeate side concentration from the predicted integral concentration is signal for a defect. By charging the permeate side volume of a porous membrane device with a gas of composition equal to that of the permeate of an integral device, a change in concentration resulting from a leak will quickly be detected.

The accelerated binary gas integrity test methods of the invention reduce the integrity testing time of porous materials by i) purging the permeate side gas with or at least near, the equilibrium concentration gas; and/or ii) reducing the permeate side gas volume; and/or increasing the permeate side gas circulation.

The following example illustrates the test time advantage of this invention. Using a binary gas mixture of 21% oxygen and 79% nitrogen (the approximate composition of air) at 40 psig as the inlet gas to a porous membrane wetted with water, the equilibrium concentration of the permeate at 15 psig is calculated to be 31.0% oxygen. Assuming a permeate side volume of 200 cm$^3$, an integral leak flow rate of 10 cm$^3$/min, a leak from the inlet side of the porous membrane of 1 cm$^3$/min, and a known initial downstream composition, the rate of composition change in the downstream volume can be calculated.

Figure 4A:
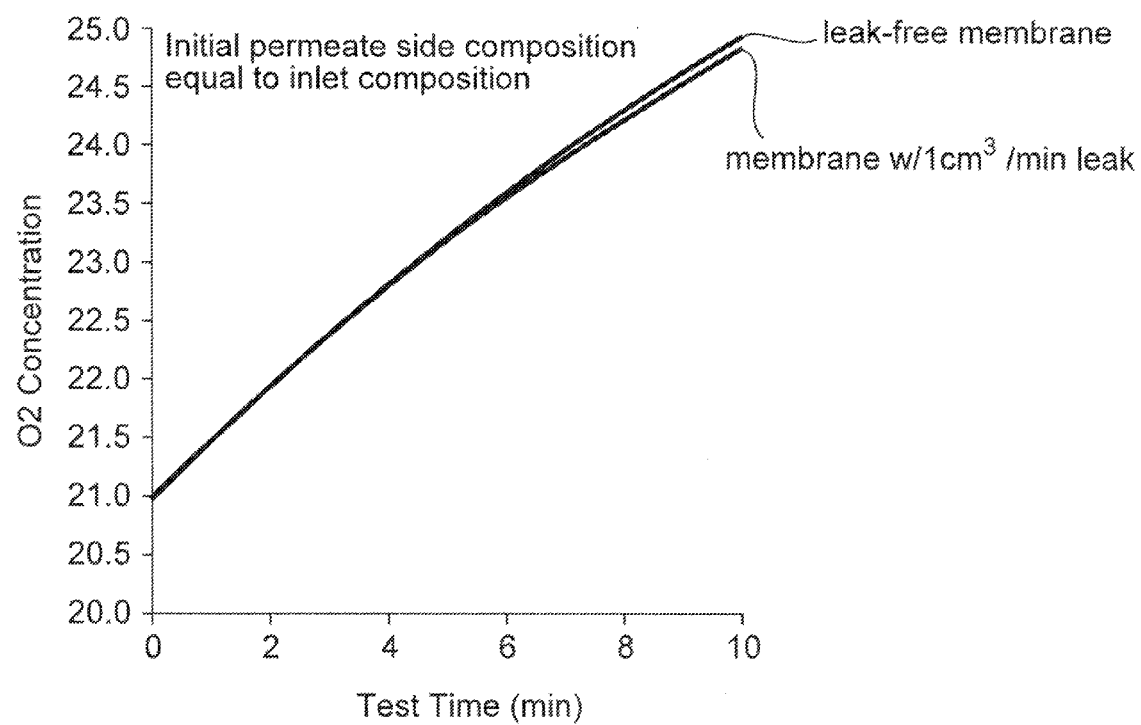
FIGS. 4A and 4B are graphs showing length of time required to find a defect in a porous material when the concentration of gas on the permeate side of the porous material is near the equilibrium value, for the feed side gas combination selected, at the start of the test. Several accelerated binary gas tests were performed on one presumed integral porous material and the impact of four variable conditions on the binary gas test output was measured. The first condition illustrates the presumed integral porous material test response generated by using the modified binary gas test setup with a laser drilled orifice of known diameter installed in the permeate side of the test with the leak valve SV-106 closed during the test. The remaining conditions show the presumed integral porous material test generated using the modified binary gas test setup with a laser drilled orifice of known diameter installed in the permeate side of the test with the leak valve (SV-106) open during the test as provided below.
Figure 4B:
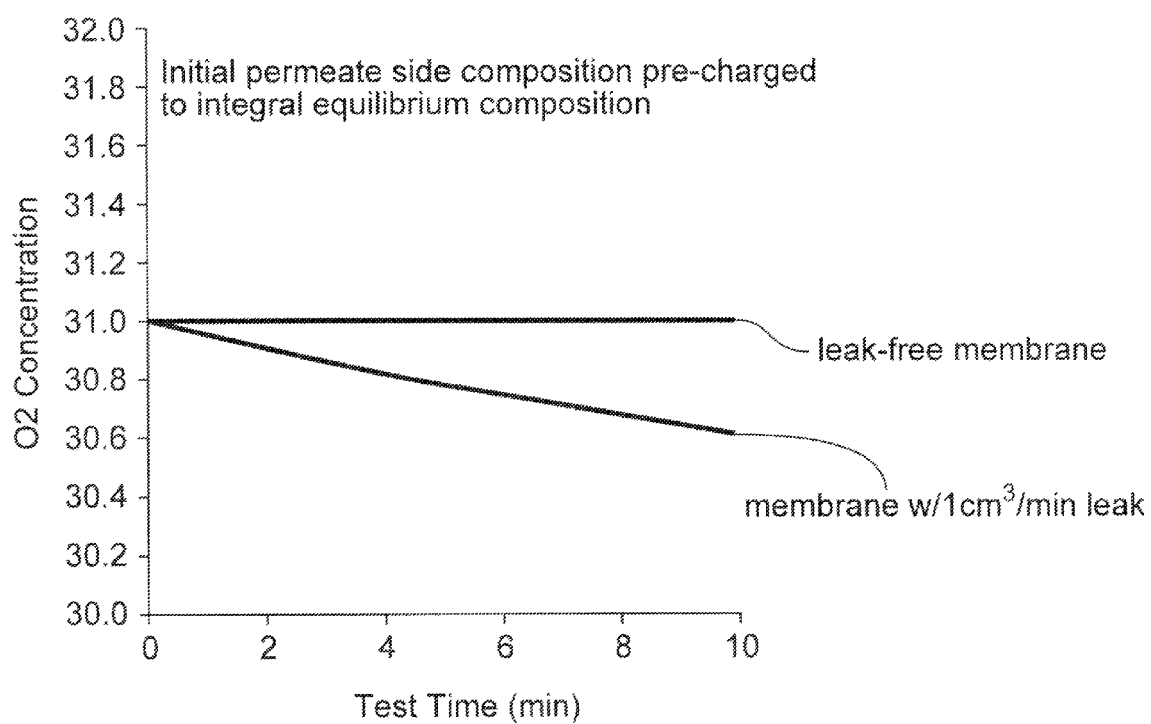

As seen in the graphs provided in FIGS. 4A and 4B, a device with 1 cm$^3$ leak is differentiated from an integral device much faster if the permeate side volume is initially charged with a gas of similar concentration to that of the equilibrium permeate gas, than one where the permeate side volume has all initial concentration that is similar to the concentration on the inlet side.

The other system components such as end caps, inlets, outlets, housings, cores, ports, valves, etc., can be made of a variety of materials, such as metal, ceramic, glass or plastic. Preferably, the components are formed of plastics, more preferably thermoplastics, such as polyolefins, especially polyethylene and polypropylene, homopolymers or copolymers thereof, ethylene vinyl acetate (EVA) copolymers; polysulfones, polyethersulfone (PES), polyarylsulfone, polyphenylsulfone, polycarbonates; styrenes; PTFE resin; thermoplastic perfluorinated polymers such PFA; nylons and other polymers.

In other embodiments, the present invention provides a method for determining the integrity of single and multilayered porous materials using an accelerated mixed gas integrity test method including the following steps:

Typical Accelerated Binary Gas Test Method

Step A. The device (EB-100) is open and ready to receive a wetted porous material (PD-100) for testing. A wetted porous material (PD-100) is loaded into the housing and the device (EB-100) is closed.

Step B. An independent air diffusion test is performed on the porous material device (PD-100). The teed side of device (EB-100) is pressurized with air from compressed gas source (CA-100) and controlled to the desired feed side to permeate side differential pressure. The process valves are switched to provide a permeate side flow path that follows from the permeate side of the porous material device (PD-100), to an absolute pressure transmitter (PT-100), to a temperature transmitter (TT-100), and through a mass flow meter (FI-101).

Step C. At the completion of the independent air diffusion test the system is prepared for an accelerated binary gas test. The feed side of device (EB-100) is depressurized and the process valves are switched to allow far equilibrium gas mixture replacement on the permeate side. The equilibrium flush gas mixture source (MG-100) is charged to the inlet side of a mass flow controller (FC-100) and the desired flush gas flow rate is set. First, the equilibrium gas mixture is flushed through the permeate side water trap valve (SV-101). The water trap valve (SV-101) is then closed, and most of the flush gas is directed through the permeate side of porous material device (PD-100); through the process condenser; through the bypass leg of the circulation loop; and out flush valve (AV-102). A portion of the equilibrium flush gas flows through the diaphragm compressor (DP-100), through the gas composition analyzer (O2-100), and is discharged to atmosphere through the flush path of the five port switching valve (AV-104).

Step D. The flush valve (AV-102) and the permeate side shutoff valve (AV-103) are closed while the equilibrium flush gas mixture source (MG-100) remains charged to the inlet side of mass flow controller (FC-100). The flush gas flow rate set point is maintained. Water trap valve (SV-101) is allowed to cycle on for a desired time, and off for a desired time to send high pressure pulses of equilibrium flush gas into, and out of the permeate side of porous material device (PD-100). The purpose of the pressure pulsing is two fold: i. to agitate the porous material pleats and remove free water and ii. to force the equilibrium flush gas into the permeate side porous material pleats.

Step E. Once the final pressure pulse in the series has been discharged to atmosphere through the drain valve (SV-101), the flush valve (AV-102) and the permeate side shutoff valve (AV-103) are opened. The drain valve (SV-101) is closed. Most of the flush gas is directed through the permeate side of porous material device (PD-100); through the process condenser; through the process leg of the circulation loop; and out flush valve (AV-102). A portion of the equilibrium flush gas flows through the diaphragm compressor (DP-100), through the gas composition analyzer (O2-100), and is discharged to atmosphere through the flush path of the five port switching valve (AV-104). At this time a feed gas from source (CA-100) is fed through a valve (AV-105); into the feed side of housing (EB-100); and through the flow control valve (MV-100) to atmosphere. An ectropneumatic regulator (I/P-101) is used to control the absolute pressure (PT-101) on the feed side of the wetted porous sample housing (EB-100) to the desired pressure ratio. The flow control valve (MV-100) is adjusted to the desired teed side sweep flow rate in order to maintain constant feed side gas concentration over the wetted porous sample (PD-100).

Step F. The flush valve (AV-102) and the permeate side shutoff valve (AV-103) are closed while the equilibrium flush gas mixture source (MG-100) remains charged to the inlet side of a mass flow controller (FC-100). The flush gas flow rate set point is maintained. Water trap valve (SV-101) is allowed to cycle on for a desired time, and off for a desired time to send high pressure pulses of equilibrium flush gas into and out of the permeate side of porous material device (PD-100).

Step G. Once the final pressure pulse in the series has been discharged to atmosphere through the drain valve (SV-101), the flush valve (AV-102) and the permeate side shutoff valve (AV-103) are opened. The drain valve (SV-101) is closed. Most of the flush gas is directed through the permeate side of porous material device (PD-100); through the process condenser; through the process leg of the circulation loop; and out flush valve (AV-102). A portion of the equilibrium flush gas flows through the diaphragm compressor (DP-100); through the gas composition analyzer (O2-100); and is discharged to atmosphere through the flush path of the five port switching valve (AV-104). This flush is considered complete when the reading on the gas composition analyzer (O2-100) is stable.

Step H. The equilibrium flush gas flow rate is ramped down to zero flow using control valve (FC-100). The permeate side loop valves are set to circulate the permeate side gas through the permeate side of the porous material sample (PD-100) and the gas composition analyzer (O2-100) for the duration of the test.

Step I. At the completion of the test the device (EB-100) is opened and the process condenser is dried. The wetted porous material (PD-100) can be removed.

Additional embodiments of the Accelerated Mixed Gas Integrity Test Systems (GIT-100) according to this invention include:

I. A device for housing a porous material sample designed to handle multiphase fluid flow on the Iced side and permeate side of the porous material in both concurrent and countercurrent flow orientations wherein:

a. the device is designed to be oriented vertically;

b. the major runs of the manifold flow path are oriented vertically;

c. the minor runs of the manifold flow path are oriented at a pitch as near to vertical as conventional machining techniques will allow;

d. the vertical and pitched nature of each run encourages gravity driven flow of liquid out of the circulation loop and into a water trap (PS-106) for isolation allowing unrestricted flow of gas through the permeate side (PS) of porous material device (PD-100) during operation. See FIG. 1, e. the device is composed of a stationary top assembly. See FIG. 1, (PS-102, PS-103, PS-105, PS-104, and PS108) and a mobile bottom assembly (PS106, PS-107, PS-109).

f. the stationary top assembly includes an outer housing (PS-108) that creates the feed side sweep flow path over a porous material device (PD-100) when mated to the mobile bottom assembly housing (PS-109);

g. the stationary top assembly includes a four part flow manifold (PS-102, PS-103, PS-104, and PS-105) used to create the permeate side (PS) recirculation loop through a porous material sample (PD-100) when mated to the mobile bottom assembly (PS-109).

II. A method for fast and repeatable exchange of the initial permeate side gas of arbitrary composition with a gas of composition at the predicted equilibrium concentration for the porous material device being tested, or near to the predicted equilibrium concentration for porous material device being tested under the test conditions selected comprising:

a. a time driven high flow rate flush of gas, of composition at the predicted equilibrium concentration for the porous material device being tested, or near to the predicted equilibrium concentration for porous material device being tested under the test conditions selected, through the permeate side water trap (PS-106) (see FIG. 1);

b. time driven high flow rate flush through the permeate side recirculation loop while bypassing the pressure transmitter (See FIG. 2);

c. a series of pressure pulses of flush gas through the permeate side recirculation loop at low feed side pressure, rapidly cycled, to deliver flush gas into, and out of the permeate side of porous material device (PD-100). The purpose of the pressure pulsing is twofold: (i.) to agitate the porous material pleats and remove free water and (ii.) to force the equilibrium flush gas into the complex geometry of the permeate side porous material pleats:

d. time driven high flow rate flush through the permeate side recirculation loop without bypassing the pressure transmitter;

e. series of pressure pulses of flush gas through the permeate side recirculation loop at high feed side pressure, rapidly cycled, to deliver flush gas into, and out of the permeate side of porous material device (PD-100). The purpose of the pressure pulsing is twofold: i. to agitate the porous material pleats and remove free water and ii. to force the equilibrium flush gas into the complex geometry of the permeate side porous material pleats; and f. a final time driven high flow rate flush through the permeate side recirculation loop without bypassing the pressure transmitter.

III. A system for repeatable control over the water vapor concentration in the permeate side (PS) recirculation loop comprising, without the use of desiccant absorber, which is a water vapor control system known to have varying rates of adsorption for different gas species when operated at non-equilibrium unsaturated conditions:

a. a process chiller (PCH-100), see FIG. 1, can be used to deliver fluid at a temperature of 0° C. to 25° C. to the transfer fluid side of a process heat exchanger sized such that the temperature of the permeate side fluid leaving the heat exchanger is approximately equal to the temperature of the transfer fluid entering the heat exchanger;

b. the permeate side (PS) fluid leaving the heat exchanger can be reheated to ambient through a short length of process piping; and c) only the concentrations of condensing species are effected in this unit operation.

In additional embodiments of the accelerated air binary gas test methods taught herein, the gas pressure may be ramped up, (e.g., slowly increased by small increments while measuring flow rate and concentration). While in other embodiments of the accelerated air binary gas test, methods taught herein, the gas pressure may be ramped down (e.g., slowly decreased by small increments while measuring flow rate and concentration).

The gas pressure may be ramped up or down in stepwise increments. Nonlimiting examples of the stepwise increments of gas pressure can be between 0.5 psi and 100 psi; or between 1 psi and 25 psi; or preferably between 5 psi and 10 psi.

The presence of a defect resulting in a permeate concentration that differs from the predicted value for an integral layer or membrane may not adversely affect the membrane performance. The accelerated air binary gas test allows defects to be quantified in terms of their size and population (number per unit area).

However, the accelerated air binary gas test methods taught herein indicate that these test methods can detect a defect in a porous material sample contributing 1.06 ml/min air flow rate, which is equivalent to about a 5.5 μm diameter defect from the choked flow model. This clearly demonstrates that the accelerated air binary gas test methods as taught herein are much more sensitive to detect a small defect than the previously known air diffusion integrity tests.

While the accelerated air binary gas integrity testing methods taught herein use two gases in the gas mixture, it should be noted that the use of more than two gases are contemplated, and that a mixture of three or more gases may be chosen by the skilled artisan.

The disclosure set forth above may encompass multiple distinct inventions with independent utility. Although each of these inventions has been disclosed and illustrated in specific embodiments, such embodiments are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A method of assessing the integrity of a porous material loaded into a porous material device using a compressed gas mixture and without the need for any gas component in the gas mixture to achieve a steady state concentration comprising
    a) loading a wetted porous material into a device having a housing for receiving the wetted porous material, resulting in a wetted porous material having a feed side and a permeate side;
    b) feeding a compressed gas mixture of two or more gas components to the feed side of the wetted porous material, wherein the feed gases have differing permeabilities in the liquid used to wet the porous material, such that one of the gases permeates through the liquid of the wetted porous material faster than the other gas or gases used;
    c) flushing out the existing gas in the permeate side volume of the porous material and replacing with a gas mixture that has a composition similar to the expected composition of permeate gas generated from an integral membrane;
    d) recirculating the permeate gas and venting excess permeate gas while maintaining a feed side gas sweep flow;
    e) assessing the concentration of the gas mixture on the permeate side; and
    f) comparing the assessed concentration of the permeate gas with the value expected from an integral device, wherein a deviation from the expected concentration by more than predetermined amount is a signal for a nonintegral porous material or porous material device.

2. The method of claim 1, wherein the liquid in (a) is water.

3. The method of claim 1, wherein at least one of the gases is $CO_2$.

4. The method of claim 1, wherein at least one of the gases is $O_2$.

5. The method of claim 1, wherein the porous material comprises a hydrophilic material.

6. The method of claim 1, wherein the porous material comprises a hydrophobic material.

7. The method of claim 1, wherein the porous material comprises a membrane.

8. The method of claim 7, wherein the membrane comprises a filtration device.

9. The method of claim 7, wherein the membrane is an asymmetric membrane.

10. The method of claim 7, wherein the membrane is a symmetric membrane.

11. The method of claim 7, wherein the membrane is comprised of a polymer.

12. The method of claim 11, wherein the polymer is PES.

13. The method of claim 7, wherein the membrane is a flat sheet in flat plate or spiral wound formats.

14. The method of claim 7, wherein the membrane is a pleated sheet, in hollow fiber or tubular formats.

15. The method of claim 1, wherein the porous material is contained in a housing.

16. The method of claim 1, wherein the porous material is contained in a cartridge.

17. The method of claim 1, wherein the porous material is a membrane comprising more than 1 layer.

18. The method of claim 1, wherein the porous material is selected from polyether sulfone, polyamide, nylon, cellulose, polytetrafluoroethylene, polysulfone, polyester, polyvinylidene fluoride, polypropylene, poly(tetrafluoroethylene-co-perfluoro(alkyl vinyl ether)), poly carbonate, polyethylene, glass fiber, polycarbonate, ceramic, and metals.

19. The method of claim 1, wherein at least one of the gases is hexafluoroethane.

20. A method of assessing the integrity of a porous material loaded into a porous material device using a compressed gas mixture and without the need for any gas component in the gas mixture to achieve a steady state concentration comprising
    a) loading a wetted porous material into a device having a housing for receiving the wetted porous material, resulting in a wetted porous material having a feed side and a permeate side;
    b) feeding a compressed gas mixture of two or more gas components wherein at least one gas is $N_2$ and the other gas is $O_2$ to the feed side of the wetted porous material, wherein the feed gases have differing permeabilities in the liquid used to wet the porous material, such that one of the gases permeates through the liquid of the wetted porous material faster than the other gas or gases used;
    c) flushing out the existing gas in the permeate side volume of the porous material and replacing with a gas mixture that has a composition similar to the expected composition of permeate gas generated from an integral membrane;
    d) recirculating the permeate gas and venting excess permeate gas while maintaining a feed side gas sweep flow;
    e) assessing the concentration of the gas mixture on the permeate side; and
    f) comparing the assessed concentration of the permeate gas with the value expected from an integral device, wherein a deviation from the expected concentration by more than predetermined amount is a signal for a nonintegral porous material or porous material device.

21. A method of assessing the integrity of a porous material loaded into a porous material device using a compressed gas mixture and without the need for any gas component in the gas mixture to achieve a steady state concentration, comprising:
   a) loading a wetted porous material into a device having a housing for receiving the wetted porous material, resulting in a wetted porous material having a feed side and a permeate side;
   b) feeding a compressed gas mixture of two or more gas components wherein at least one gas is hexafluoroethane and the other gas is $CO_2$ to the feed side of the wetted porous material, wherein the feed gases have differing permeabilities in the liquid used to wet the porous material, such that one of the gases permeates through the liquid of the wetted porous material faster than the other gas or gases used;
   c) flushing out the existing gas in the permeate side volume of the porous material and replacing with a gas mixture that has a composition similar to the expected composition of permeate gas generated from an integral membrane;
   d) recirculating the permeate gas and venting excess permeate gas while maintaining a feed side gas sweep flow;
   e) assessing the concentration of the gas mixture on the permeate side; and
   f) comparing the assessed concentration of the permeate gas with the value expected from an integral device, wherein a deviation from the expected concentration by more than predetermined amount is a signal for a non-integral porous material or porous material device.

22. A method of assessing the integrity of a porous material loaded into a porous material device using a compressed gas mixture and without the need for any gas component in the gas mixture to achieve a steady state concentration, comprising:
   a) loading a wetted porous material into a device having a housing for receiving the wetted porous material, resulting in a wetted porous material having a feed side and a permeate side;
   b) feeding a compressed gas mixture of two or more gas components wherein at least one gas is $CO_2$ and the other gas is $O_2$ to the feed side of the wetted porous material, wherein the feed gases have differing permeabilities in the liquid used to wet the porous material, such that one of the gases permeates through the liquid of the wetted porous material faster than the other gas or gases used;
   c) flushing out the existing gas in the permeate side volume of the porous material and replacing with a gas mixture that has a composition similar to the expected composition of permeate gas generated from an integral membrane;
   d) recirculating the permeate gas and venting excess permeate gas while maintaining a feed side gas sweep flow;
   e) assessing the concentration of the gas mixture on the permeate side; and
   f) comparing the assessed concentration of the permeate gas with the value expected from an integral device, wherein a deviation from the expected concentration by more than predetermined amount is a signal for a non-integral porous material or porous material device.

* * * * *